(12) United States Patent
Gerard et al.

(10) Patent No.: US 7,230,229 B2
(45) Date of Patent: Jun. 12, 2007

(54) METHOD AND DEVICE FOR THE DETECTION OF SURFACE DEFECTS ON THE OUTER WALL OF A TRANSPARENT OR TRANSLUCENT OBJECT

(75) Inventors: Marc Gerard, Givors (FR); Guillaume Bathelet, Lyons (FR)

(73) Assignee: Tiama, Montagny (FR)

( * ) Notice: Subject to any disclaimer, the term of this patent is extended or adjusted under 35 U.S.C. 154(b) by 22 days.

(21) Appl. No.: 10/532,613

(22) PCT Filed: Oct. 24, 2003

(86) PCT No.: PCT/FR03/03165

§ 371 (c)(1),
(2), (4) Date: Nov. 18, 2005

(87) PCT Pub. No.: WO2004/040277

PCT Pub. Date: May 13, 2004

(65) Prior Publication Data

US 2006/0124872 A1    Jun. 15, 2006

(30) Foreign Application Priority Data

Oct. 25, 2002    (FR) .................................. 02 13361

(51) Int. Cl.
*G01N 9/04*  (2006.01)
(52) U.S. Cl. ................. 250/223 B; 250/559.4
(58) Field of Classification Search ............ 250/223 B, 250/223 R, 221, 559.4, 559.44, 208.1; 356/240.1, 356/237.2, 237.5
See application file for complete search history.

(56) References Cited

U.S. PATENT DOCUMENTS

| | | | |
|---|---|---|---|
| 4,584,469 A | * | 4/1986 | Lovalenti ................ 250/223 B |
| 5,258,611 A | | 11/1993 | Leser |
| 5,637,864 A | | 6/1997 | Nicks et al. |
| 6,369,889 B1 | | 4/2002 | Olschewski |

FOREIGN PATENT DOCUMENTS

EP    1118854 A1    7/2001

* cited by examiner

*Primary Examiner*—Que T. Le
(74) *Attorney, Agent, or Firm*—Clark & Brody

(57) ABSTRACT

The device for detecting surface defects on the outer wall (2) of a transparent or translucent object (3), comprises:
  a broad light source (4), adapted to send a light beam (5) onto a surface of the wall (2),
  a linear sensor (8) for measuring light beams, arranged to collect the light beam (9) reflected by a linear zone of the wall (2), illuminated by the light source (4),
  means (12) ensuring relative movement between the object and the light source (4) and the linear measuring sensor (8), to move the linear measuring zone over the wall (2) of the object to cover the surface to be inspected,
  and a unit (15) for analysing and processing the light beams, received by the measuring sensor (8), for creating an image and to identify within the image the presence of a surface defect corresponding to a dark area.

12 Claims, 1 Drawing Sheet

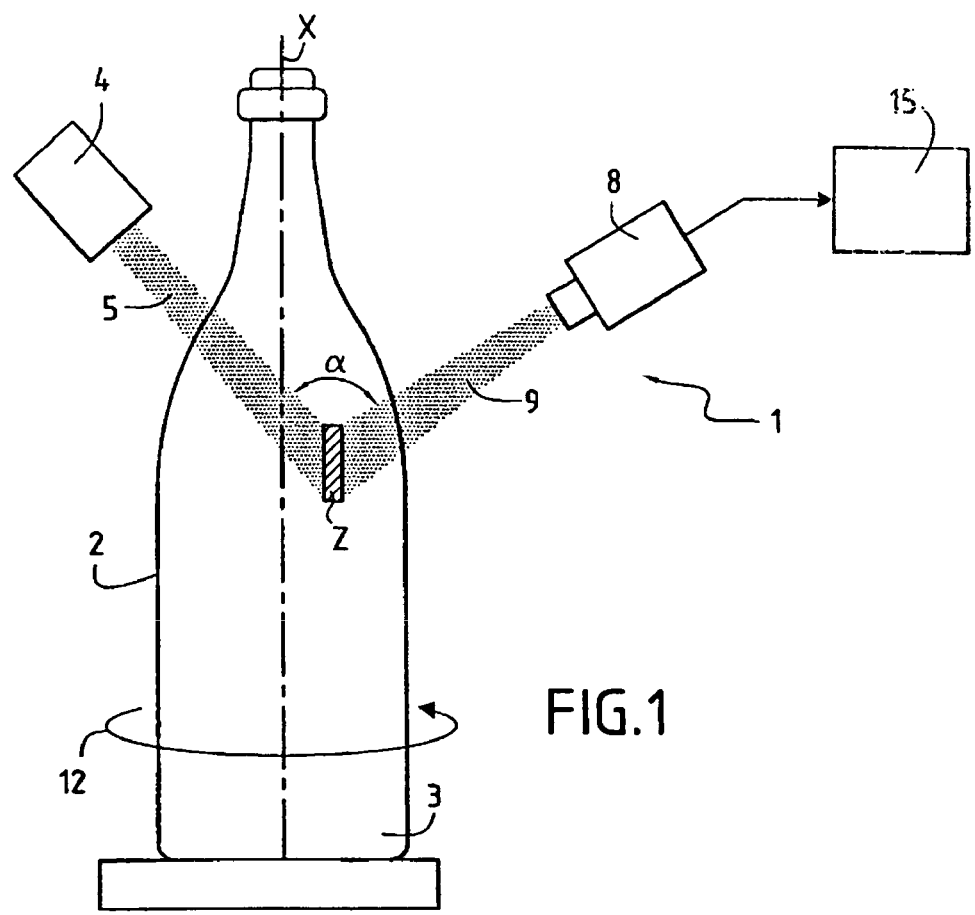
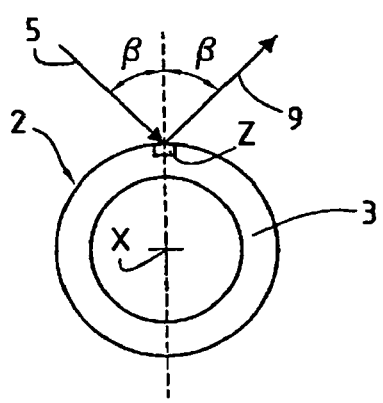
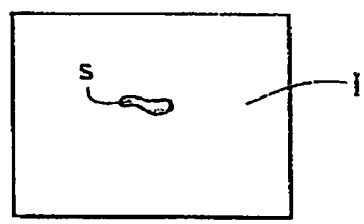
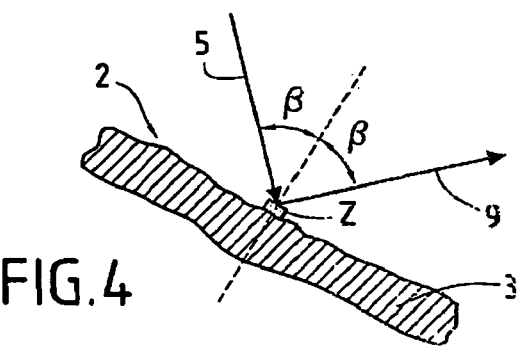

METHOD AND DEVICE FOR THE DETECTION OF SURFACE DEFECTS ON THE OUTER WALL OF A TRANSPARENT OR TRANSLUCENT OBJECT

FIELD OF THE INVENTION

The present invention pertains to the technical area of the opto-electronical inspection of objects in general, such as planar items or containers such as bottles, jars, or flasks, that are transparent or translucent, for the purpose of detecting any surface defects on a transparent or translucent object.

BACKGROUND OF THE INVENTION

The subject of the invention is more precisely to detect any surface defects on a transparent or translucent object, such as wrinkles, washboards, load marks or neck ring flaws.

In the state of the art, a device is known to detect said defects comprising a diffuse light source which illuminates an object to be inspected. One or more cameras are arranged opposite the light source to collect the light flow transmitted through the object. Any defects in the object attenuate or deviate the transmitted light. These light variations are analysed to identify and detect defects. Said device is particularly adapted for visualizing and detecting inner defects on the side wall of the object. However, with said device it is not possible to visualize and detect minor, transparent surface defects.

Also, a technique is known, in particular through documents U.S. Pat. No. 5,637,864, or EP 1 118 854, which illuminates defects for their detection. However, this technique is not suitable for detecting surface defects that are transparent.

BRIEF SUMMARY OF THE INVENTION

The present invention sets out to overcome the prior art drawbacks by proposing a technical solution for detecting surface defects, transparent defects in particular, on the outer wall of a transparent or translucent object.

To attain this objective, the invention proposes a method for detecting surface defects on the outer wall of a transparent or translucent object, which comprises the following steps:
 by means of a uniform, extensive, broad light source, sending an incident light beam onto a surface of the outer wall of an object,
 arranging a linear measuring sensor to collect the light beam reflected by a linear zone of the outer wall, illuminated by the light source,
 ensuring relative movement between firstly the object and secondly the light source and linear measuring sensor, so as to move the linear measuring zone over the outer wall of the object to cover the surface to be inspected,
 processing the light beams received by the linear sensor, so as to create an image and identify, within the image, the presence of any surface defect corresponding to a dark area.

According to one preferred characteristic of embodiment, the method consists of sending an incidence light beam onto the surface of the outer wall of the object, the angle of incidence being adapted to ensure optimum reflection of the incident light beam.

According to another preferred characteristic of embodiment, the method consists of arranging the linear measuring sensor to collect the beam reflected at an angle of reflection of equal value to the angle of incidence.

According to one advantageous characteristic of the invention, for an object of revolution having an axis of symmetry, the method consists of:
 choosing, as linear zone of the outer wall of the object, at least part of a generatrix parallel to the axis of symmetry,
 ensuring movement of the object about its axis of symmetry through a complete rotation.

A further subject of the invention is to propose a device for detecting surface defects on the outer wall of a transparent or translucent object. The device of the invention comprises:
 a uniform, extensive, broad light source adapted for sending an incident light beam onto a surface of the outer wall of the object,
 a linear sensor for measuring light beams, arranged to collect the light beam reflected by a linear zone of the outer wall, illuminated by the light source,
 means ensuring relative movement between firstly the object and secondly the light source and linear measuring sensor so as to move the linear measuring zone over the outer wall of the object to cover the surface to be inspected,
 and a unit for analyzing and processing the light beams received by the measuring sensor, adapted to create an image and to identify within the image the presence of any surface defect corresponding to a dark area.

According to one preferred characteristic of embodiment, the detection device comprises a light source positioned relative to the object so that the incident light beam forms an incident angle adapted to ensure optimum reflection of the incident light beam.

According to another characteristic of embodiment, the linear measuring sensor is positioned relative to the object to collect the beam reflected at an angle of reflection of equal value to the angle of incidence.

According to a further advantageous characteristic of embodiment, the detection device of the invention, the light source and the linear measuring sensor are positioned to send the incident light beam and collect the reflected light beam respectively, for a linear zone of the outer wall of the object forming at least part of a generatrix of an object of revolution having an axis of symmetry, the movement means ensuring movement of the object about its axis of symmetry through a complete rotation.

Various other characteristics will become apparent in the following description with reference to the appended drawings showing non-limitative examples of embodiment of the subject of the invention.

BRIEF DESCRIPTION OF THE DRAWINGS

FIG. 1 is a perspective view illustrating the operating principle of the device of the invention.

FIG. 2 is a cross-sectional view showing the direction of the light beams according to the method of the invention.

FIG. 3 shows an example of an image obtained using the device of the invention.

FIG. 4 is a cross-section showing another example applying the subject of the invention to the detection of defects on a planar wall.

As can be seen more precisely in FIGS. 1 to 3, the subject of the invention concerns a method with which it is possible, by means of device 1, to detect surface defects on the outer wall 2 of a transparent or translucent object 3. In the example of embodiment shown FIGS. 1 to 3, the transparent or translucent object 3 is an object of revolution, such as a bottle, jar or flask having an axis of symmetry or revolution X.

DETAILED DESCRIPTION OF THE INVENTION

Device 1 of the invention comprises a light source 4 designed to deliver diffuse light or light of wide expanse having a uniform or homogenous nature. This light source 4 is adapted to send an incident light beam 5 onto a surface of the outer wall 2 of object 3.

Device 1 of the invention also comprises a linear measuring sensor 8, such as a line scan camera able to collect the beam 9 reflected by a linear zone Z of the outer wall 2, illuminated by the light source 4. The sighting axis of the measuring camera 8, schematised by the reflected beam 9, forms an angle α with the corresponding incident light beam emitted by the light source 4. The light source 4 is positioned, with respect to object 3, so that the incident light beam 5 forms an angle of incidence that is adapted to ensure optimum reflection of the incident beam.

Similarly, camera 8 is positioned so as to collect the light beam reflected by the linear zone Z of the outer wall 2 of the object and illuminated by light source 4. In this respect, the line of photosensitive cells of camera 8 is evidently oriented along an axis parallel to the linear zone Z of the outer wall to be inspected 2. According to a preferred characteristic of the embodiment illustrated in FIG. 2, the camera 8 is positioned to visualize a linear zone Z corresponding to at least part of a generatrix G parallel to the axis of symmetry X of the object of revolution. In this preferred example of embodiment, object 3 is moved rotationally about its axis of symmetry X through a complete rotation of object 3, so as to enable inspection of the entire outer surface of object 3.

As can be seen more precisely in FIG. 2, the linear measuring sensor 8, which collects the reflected light beam 9, is positioned relative to the normal to linear zone Z of the outer wall 2 of the object, at an angle of reflection β of equal value to the angle of incidence β lying between the normal to the surface of linear zone Z and the incident light beam 5.

In the illustrated example, the device also comprises means 12 ensuring the relative movement between firstly the object 3 and secondly the source 4 and the linear measuring sensor 8, so as to move the linear measuring zone Z over the outer wall 2 of the object. In the illustrated example, the movement means 12 enable rotation of the object about its axis of revolution through a complete revolution so as to scan the entirety of the surface of the outer wall 2.

The device of the invention also comprises a unit 15 for analysing and processing the light beams received by the measuring sensor 8. This analysis and processing unit 15 is adapted to create an image and to identify, within the image, the presence of a surface defect corresponding to a dark area. It is to be considered that camera 8 delivers electronic signals representing the light intensity received by each of the photosensitive cells of camera 8. The analysis and processing unit 15 ensures conversion of the analogue signal into a digital signal coded on a certain number of bits in accordance with a determined scale of grey tones. From these signals, an image is generated then filtered to obtain a final image I, such as illustrated FIG. 3. Since the presence of a surface defect eliminates reflection, a surface defect is therefore characterized by the presence of a dark area s in the image. Unit 15 analyses this image to calculate preset characteristics such as position in space, surface, perimeter, centre of gravity or grey level of the dark area s. These measured characteristics are then compared with threshold values to determine whether or not said dark area s corresponds to a defect.

In the preceding description, the object to be inspected 3 is an object of revolution. Evidently, the present invention may be applied to an object, for example a planar object, whose outer wall 2 is to be inspected (FIG. 4). The subject of the invention, such as described above, may be applied by sending an incident light beam 5 onto the surface of the wall 2 of the object and by arranging a linear measuring sensor 8 to collect the light beam 9 reflected by a linear zone Z of the outer wall 2, illuminated by the light source 4. Preferably, the linear measuring sensor 8 is positioned with respect to the normal to the surface, at an angle of reflection β of equal value to the angle of incidence β formed by the incident light beam 5. The surface of wall 2 is moved linear fashion so that it is possible to scan the compete surface of object 3.

With the subject of the invention, it is therefore possible to reliably detect surface defects that are difficult to detect such as minor transparent surface defects. The relative positioning of light source 4 and sensor 8 is such that it is possible to achieve maximum contrasting of the sought defect with the reflected light 9.

The invention is not limited to the examples shown and described since various modifications may be made thereto while remaining within the scope of the invention.

The invention claimed is:

1. Method for detecting surface defects on the outer wall (2) of a transparent or translucent object (3), characterized in that it comprises the following steps:
   by means of a uniform, extensive, broad light source (4), sending an incident light beam (5) onto a surface of the outer wall (2) of the object,
   arranging a linear measuring sensor (8) to collect the light beam (9) reflected by a linear zone (Z) of the outer wall (2), illuminated by the light source (4),
   ensuring relative movement between firstly the object (3) and secondly the light source (4) and the linear measuring sensor (8), so as to move the linear measuring zone (Z) over the outer wall (2) of the object to cover the surface to be inspected,
   and processing the light beams (9) received by the linear sensor, so as to create an image (I) and to identify within the image the presence of a surface defect corresponding to a dark area (s).

2. Method as in claim 1, characterized in that it consists of sending onto the surface of the outer wall (2) of the object an incident light beam (5) having an angle of incidence adapted to ensure optimum reflection of the incident light beam.

3. Method as in claim 1, characterized in that it consists of arranging the linear measuring sensor (8) to collect the beam reflected at an angle of reflection (β) of equal value to the angle of incidence (β).

4. Method as in claim 1, characterized in that for an object of revolution (3) having an axis of symmetry (X), it consists of:
   choosing, as linear zone (Z) of the outer wall (2) of the object, at least part of a generatrix (G) parallel to the axis of symmetry (X),
   ensuring movement of the object (3) about its axis of symmetry (X) through a complete rotation.

5. Device for detecting surface defects on the outer wall (2) of a transparent or translucent object (3), characterized in that it comprises:
- a uniform, extensive, broad light source (4), adapted to send an incident light beam (5) onto a surface of the outer wall (2) of the object,
- a linear sensor (8) to measure light beams, arranged to collect the light beam (9) reflected by a linear zone (Z) of the outer wall (2), illuminated by the light source (4),
- means (12) ensuring relative movement between firstly the object and secondly the light source (4) and the linear measuring sensor (8), so as to move the linear measuring zone (Z) over the outer wall (2) of the object to cover the surface to be inspected,
- and a unit (15) for a analysing and processing the light beams received by the measuring sensor (8), adapted to create an image (I) and to identify, within the image, the presence of a surface defect corresponding to a dark area (s).

6. Device as in claim 5, characterized in that the light source (4) is positioned, relative to object (3), so that the incident light beam (5) forms an incident angle that is adapted to ensure optimum reflection of the incident light beam.

7. Device as in claim 5, characterized in that the linear measuring sensor (8) is positioned with respect to object (3), to collect the beam reflected at an angle of reflection ($\beta$) of equal value to the angle of incidence ($\beta$).

8. Device as in claim 5, characterized in that the light source (4) and the linear measuring sensor (8) are positioned to respectively send an incident light beam (5) and collect the reflected light beam (9), for a linear zone (Z) of the outer wall of the object forming at least part of a generatrix (G) of an object of revolution having an axis symmetry (X), and in that the movement means (12) ensure movement of the object (3) about its axis of symmetry (X) through a complete rotation.

9. Method as in claim 2, characterized in that it consists of arranging the linear measuring sensor (8) to collect the beam reflected at an angle of reflection ($\beta$) of equal value to the angle of incidence ($\beta$).

10. Device as in claim 6, characterized in that the linear measuring sensor (8) is positioned with respect to object (3), to collect the beam reflected at an angle of reflection ($\beta$) of equal value to the angle of incidence ($\beta$).

11. Device as in claim 6, characterized in that the light source (4) and the linear measuring sensor (8) are positioned to respectively send an incident light beam (5) and collect the reflected light beam (9), for a linear zone (Z) of the outer wall of the object forming at least part of a generatrix (G) of an object of revolution having an axis symmetry (X), and in that the movement means (12) ensure movement of the object (3) about its axis of symmetry (X) through a complete rotation.

12. Device as in claim 7, characterized in that the light source (4) and the linear measuring sensor (8) are positioned to respectively send an incident light beam (5) and collect the reflected light beam (9), for a linear zone (Z) of the outer wall of the object forming at least part of a generatrix (G) of an object of revolution having an axis symmetry (X), and in that the movement means (12) ensure movement of the object (3) about its axis of symmetry (X) through a complete rotation.

* * * * *